US010746859B2

(12) United States Patent
Robert et al.

(10) Patent No.: US 10,746,859 B2
(45) Date of Patent: Aug. 18, 2020

(54) SYSTEM AND METHOD FOR ACOUSTIC IMAGING WITH COHERENT COMPOUNDING USING INTERCOSTAL SPACES

(71) Applicant: KONINKLIJKE PHILIPS N.V., Eindhoven (NL)

(72) Inventors: Jean-Luc Robert, Cambridge, MA (US); Emil George Radulescu, Ossining, NY (US); Francois Guy Gerard Marie Vignon, Croton on Hudson, NY (US)

(73) Assignee: Koninklijke Philips N.V., Eindhoven (NL)

(*) Notice: Subject to any disclaimer, the term of this patent is extended or adjusted under 35 U.S.C. 154(b) by 633 days.

(21) Appl. No.: 15/300,143

(22) PCT Filed: Mar. 18, 2015

(86) PCT No.: PCT/IB2015/051972
§ 371 (c)(1),
(2) Date: Sep. 28, 2016

(87) PCT Pub. No.: WO2015/150954
PCT Pub. Date: Oct. 8, 2015

(65) Prior Publication Data
US 2017/0184713 A1 Jun. 29, 2017

Related U.S. Application Data
(60) Provisional application No. 61/972,896, filed on Mar. 31, 2014.

(51) Int. Cl.
G01S 7/52 (2006.01)
A61B 8/08 (2006.01)
(Continued)

(52) U.S. Cl.
CPC ........ *G01S 7/52047* (2013.01); *A61B 8/4483* (2013.01); *A61B 8/5269* (2013.01);
(Continued)

(58) Field of Classification Search
CPC ............. G01S 7/52047; G01S 15/8927; G01S 15/8997; G01S 15/8977; A61B 8/4483; A61B 8/5269
See application file for complete search history.

(56) References Cited

U.S. PATENT DOCUMENTS 5,278,757 A * 1/1994 Hoctor ............... G01S 15/8997
600/459
5,640,959 A 6/1997 Yasushi et al.
(Continued)

FOREIGN PATENT DOCUMENTS

CN 103565473 A 2/2014
WO 2008051639 A2 5/2008

OTHER PUBLICATIONS

Martin CJ, Martinez-Graullera O, Godoy G, Ullate LG. Coarray Synthesis Based on Polynomial Decomposition 2010. IEEE transactions on image processing. Apr. 2010;19(4):1102-7. (Year: 2010).*
(Continued)

*Primary Examiner* — Amanda Lauritzen Moher

(57) ABSTRACT

An apparatus and method of imaging an imaging region (7) employ an acoustic transducer array (10') to produce image data for the imaging region (7), wherein there are one or more obstructions (15-1, 15-2, 15-3) between the acoustic transducer array (10') and at least a portion (5) of the imaging region (7). One or more processors exploit redundancy in transmit/receive pair paths among the acoustic transducers in the acoustic transducer array (10') to compensate for missing image data of the imaging region (7) due to the one or more obstructions (15-1, 15-2, 15-3), and
(Continued)

produce an image of the imaging region (7) from the compensated image data.

14 Claims, 16 Drawing Sheets

(51) Int. Cl.
*A61B 8/00* (2006.01)
*G06T 5/00* (2006.01)
*G01S 15/89* (2006.01)
*G06T 7/00* (2017.01)

(52) U.S. Cl.
CPC ...... *G01S 15/8927* (2013.01); *G01S 15/8977* (2013.01); *G01S 15/8997* (2013.01); *G06T 5/00* (2013.01); *G06T 7/0012* (2013.01)

(56) References Cited

U.S. PATENT DOCUMENTS

| | | | | |
|---|---|---|---|---|
| 2005/0015010 A1* | 1/2005 | Antich | ............... | A61B 5/0048 600/449 |
| 2005/0124883 A1* | 6/2005 | Hunt | ............... | A61B 8/08 600/437 |
| 2012/0095343 A1* | 4/2012 | Smith | ............... | A61B 8/58 600/447 |
| 2012/0302927 A1* | 11/2012 | Khokhlova | ............. | A61N 7/02 601/2 |
| 2013/0077441 A1* | 3/2013 | Ramamurthy | ........... | A61B 8/08 367/87 |
| 2013/0253325 A1 | 9/2013 | Call et al. | | |
| 2014/0031689 A1 | 1/2014 | Kang et al. | | |

OTHER PUBLICATIONS

Weisstein, Eric W. "Apodization Function." From MathWorld—A Wolfram Web Resource. Page date: Aug. 11, 2018. http://mathworld.wolfram.com/ApodizationFunction.html (Year: 2018).*

Vyas et al. "Ultrasound Beam Simulations in Inhomogeneous Tissue Geometries Using the Hybrid Angular Spectrum Method." IEEE Transactions on Ultrasonics, Ferroelectrics, and Frequency Control 59(6): 1093-1100. Jun. 2012.*

Lovstakken, et al., "Real-time Indication of Acoustic Window for Phased-Array Transducers in Ultrasound Imaging", 2007 IEEE Ultrasonics Symposium, Oct. 1, 2007, pp. 1549-1552.

Kortbek, et al., "Synthetic Aperture Sequential Beamforming", 2008 IEEE International Ultrasonics Symposium Proceedings, Nov. 2, 2008, pp. 966-969.

* cited by examiner

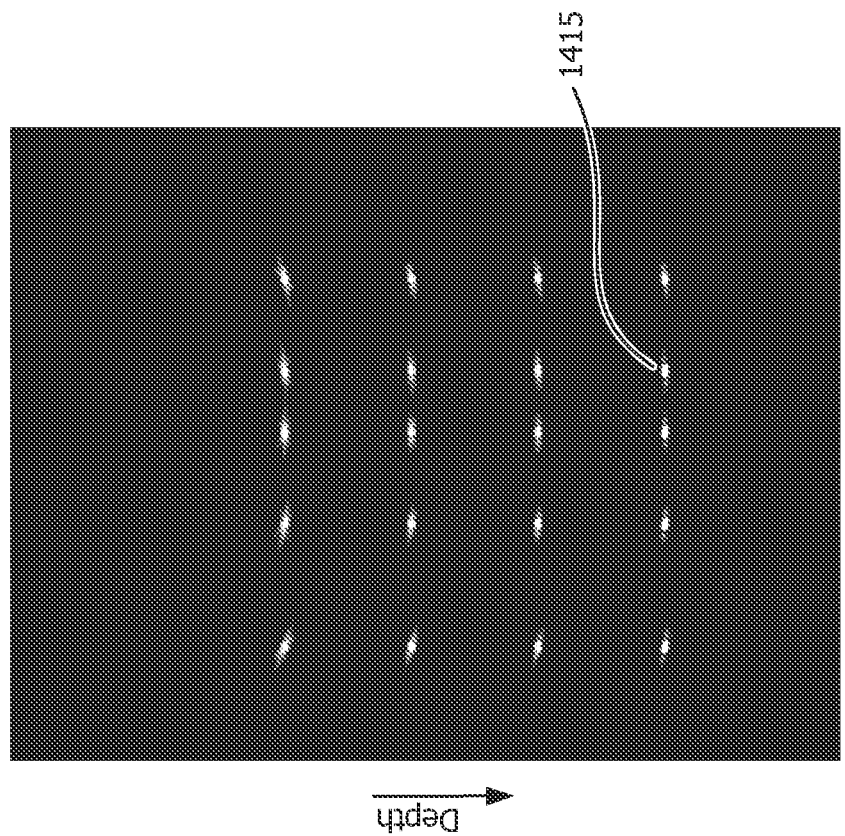
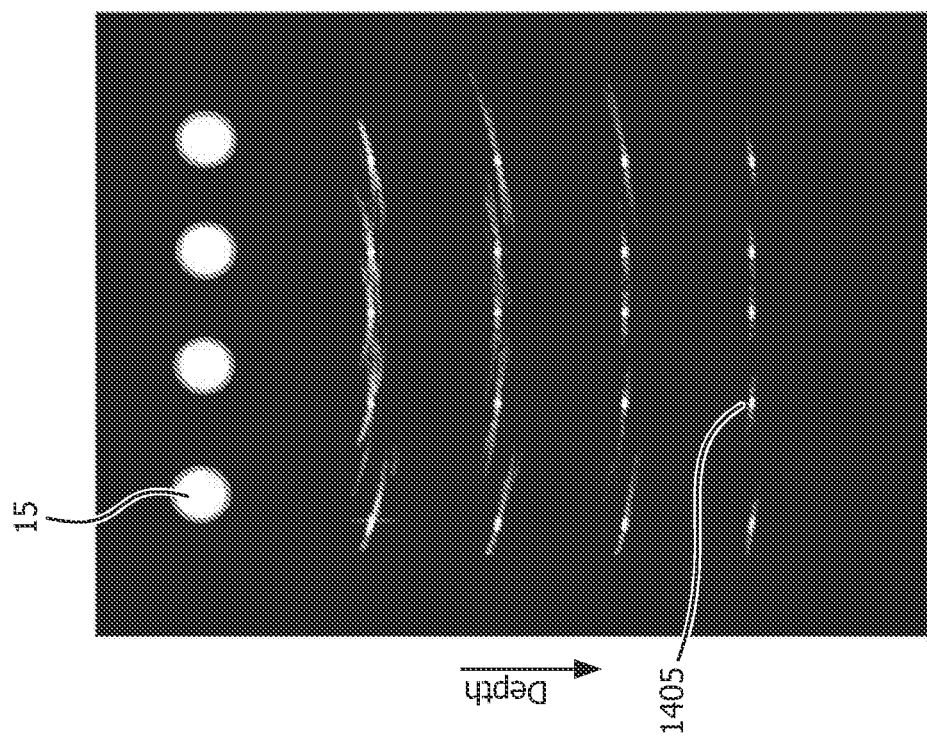
FIG. 14B
FIG. 14A

SYSTEM AND METHOD FOR ACOUSTIC IMAGING WITH COHERENT COMPOUNDING USING INTERCOSTAL SPACES

This application is the U.S. National Phase application under 35 U.S.C. § 371 of International Application No. PCT/IB2015/051972, filed on Mar. 18, 2015, which claims the benefit of Provisional Application Ser. No. 61/972,896, filed Mar. 31, 2014. These applications are hereby incorporated by reference herein.

TECHNICAL FIELD

This invention relates to acoustic imaging apparatuses, systems and methods.

BACKGROUND AND SUMMARY

In acoustic (e.g., ultrasound) imaging, or other active acoustics imaging, an array of transducers first transmits a pulse into the medium, usually with appropriate delay to generate a focused beam, and then receives the echo. Beamforming is used to reconstruct an image of the medium. The quality of the image is related to the point-spread function (PSF), or response of the imaging system to a single point. The PSF is related to the aperture of the array. In the far field approximation, the lateral profile of the PSF is the square of the Fourier transform of the aperture amplitude distribution. If no apodization is used it would be a $sinc^2$ function.

However part of the aperture may be blocked by one or several obstacles. In medical ultrasound, the obstacle could be a rib. For example, ultrasound imaging of the heart through the chest (transthoracic ultrasound imaging) is complicated by the presence of ribs which may block part of the aperture if it is too large. If the blocked part of the aperture is along the edge of the aperture, this will result in a loss of resolution. If it is within the aperture, it will result in grating lobes that may severely reduce the image quality. The same phenomenon results from a gap in the aperture, which can be caused by non-functioning transducer array elements, or if one attempts to image coherently with two ultrasound arrays that are separated by a gap. On the other hand, if a smaller aperture is employed which fits in the space between two ribs (hereafter referred to as an "intercostal gap"), then the field of view and resolution of the ultrasound image is limited.

Accordingly, it would be desirable to provide a method and system for ultrasound imaging which can use a larger coherent aperture across several intercostal spaces.

In one aspect of the invention, a method comprises: employing an acoustic transducer array to produce image data for the imaging region, wherein there are one or more obstructions between the acoustic transducer array and at least a portion of the imaging region; exploiting redundancy in transmit/receive pair paths among the acoustic transducers in the acoustic transducer array to compensate for missing image data of the imaging region due to the one or more obstructions; and producing an image of the imaging region from the compensated image.

In some embodiments, exploiting redundancy in transmit/receive pair paths among the acoustic transducers in the acoustic transducer array to compensate for missing image data of the imaging region due to the one or more obstructions and producing an image of the imaging region from the compensated image data comprises: determining an inverse filter for the acoustic transducer array, wherein when the inverse filter is multiplied by an angular spectrum for the acoustic transducer array with respect to the imaging region in the presence of the one or more obstructions, it produces an ideal angular spectrum for the acoustic transducer array with respect to the imaging region which would exist in the absence of the one or more obstructions; weighting a signal produced by each transmit/receive pair of elements in the acoustic transducer array by a value of the inverse filter corresponding to the angular frequency of the transmit/receive pair, and generating an acoustic image by summing the weighted signals of all the transmit receive pairs.

In some embodiments, exploiting redundancy in transmit/receive pair paths among the acoustic transducers in the acoustic transducer array to compensate for missing image data of the imaging region due to the one or more obstructions and producing an image of the imaging region from the compensated image data comprises: performing at least first and second transmit-and-receive operations using at least first and second apodization functions, including: performing the first transmit-and-receive operation by employing the acoustic transducer array to transmit a first acoustic wave to the imaging region and to receive back from the imaging region a first acoustic echo and to produce therefrom first image data, wherein the first apodization function is applied to the acoustic transducer array to produce a first transmit aperture and a first receive aperture for the first transmit-and-receive operation, and performing the second transmit-and-receive operation by employing the acoustic transducer array to transmit a second acoustic wave to the imaging region and to receive back from the imaging region a second acoustic echo and to produce therefrom second image data, wherein the second apodization function is applied to the acoustic transducer array to produce a second transmit aperture and a second receive aperture for the second transmit-and-receive operation; and producing an image of the imaging region by combining the first image data with the second image data. The at least first and second apodization functions are determined from an inverse filter for the acoustic transducer array with respect to the imaging region, wherein when the inverse filter is multiplied by an angular spectrum for the acoustic transducer array with respect to the imaging region in the presence of the one or more obstructions, it produces an ideal angular spectrum for the acoustic transducer array with respect to the imaging region which would exist in the absence of the one or more obstructions.

In some embodiments, exploiting redundancy in transmit/receive pair paths among the acoustic transducers in the acoustic transducer array to compensate for missing image data of the imaging region due to the one or more obstructions and producing an image of the imaging region from the compensated image data comprises performing an RF data (pre-detection) based or image based deconvolution algorithm.

In another aspect of the invention, an apparatus for imaging an imaging region, comprises: an acoustic transducer array configured to produce image data for the imaging region, wherein there are one or more obstructions between the acoustic transducer array and at least a portion of the imaging region; and one or more processors, configured to exploit redundancy in transmit/receive pair paths among the acoustic transducers in the acoustic transducer array to compensate for missing image data of the imaging region due to the one or more obstructions, and to produce an image of the imaging region from the compensated image data.

In some embodiments, the one or more processors are configured to exploit redundancy in transmit/receive pair paths among the acoustic transducers in the acoustic transducer array to compensate for missing image data of the imaging region due to the one or more obstructions, and to produce an image of the imaging region from the compensated image data, by: determining an inverse filter for the acoustic transducer array, wherein when the inverse filter is multiplied by an angular spectrum for the acoustic transducer array with respect to the imaging region in the presence of the one or more obstructions, it produces an ideal angular spectrum for the acoustic transducer array with respect to the imaging region which would exist in the absence of the one or more obstructions; weighting a signal produced by each transmit/receive pair of elements in the acoustic transducer array by a value of the inverse filter corresponding to the angular frequency of the transmit/receive pair, and generating an acoustic image by summing the weighted signals of all the transmit receive pairs.

In some embodiments, the one or more processors are configured to exploit redundancy in transmit/receive pair paths among the acoustic transducers in the acoustic transducer array to compensate for missing image data of the imaging region due to the one or more obstructions, and produce an image of the imaging region from the compensated image data, by: performing at least first and second transmit-and-receive operations using at least first and second apodization functions, including: performing the first transmit-and-receive operation by employing the acoustic transducer array to transmit a first acoustic wave to the imaging region and to receive back from the imaging region a first acoustic echo and to produce therefrom first image data, wherein the first apodization function is applied to the acoustic transducer array to produce a first transmit aperture and a first receive aperture for the first transmit-and-receive operation, and performing the second transmit-and-receive operation by employing the acoustic transducer array to transmit a second acoustic wave to the imaging region and to receive back from the imaging region a second acoustic echo and to produce therefrom second image data, wherein the second apodization function is applied to the acoustic transducer array to produce a second transmit aperture and a second receive aperture for the second transmit-and-receive operation; and producing an image of the imaging region by combining the first image data with the second image data. The at least first and second apodization functions are determined from an inverse filter for the acoustic transducer array with respect to the imaging region, wherein when the inverse filter is multiplied by an angular spectrum for the acoustic transducer array with respect to the imaging region in the presence of the one or more obstructions, it produces an ideal angular spectrum for the acoustic transducer array with respect to the imaging region which would exist in the absence of the one or more obstructions.

In some embodiments, the one or more processors are configured to exploit redundancy in transmit/receive pair paths among the acoustic transducers in the acoustic transducer array to compensate for missing image data of the imaging region due to the one or more obstructions and producing an image of the imaging region from the compensated image data by performing an RF data (pre-detection) based or image based deconvolution algorithm.

BRIEF DESCRIPTION OF THE DRAWINGS

FIG. 14A illustrates an image produced in the presence of ribs similar to that show in FIG. 13, when coherent compounding using an "intercostal gap compensation" algorithm is employed.

FIG. 14B illustrates an image similar to that show in FIGS. 13 and 14A which would be produced in the absence of any ribs.

DETAILED DESCRIPTION

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided as teaching examples of the invention.

Figure 1:
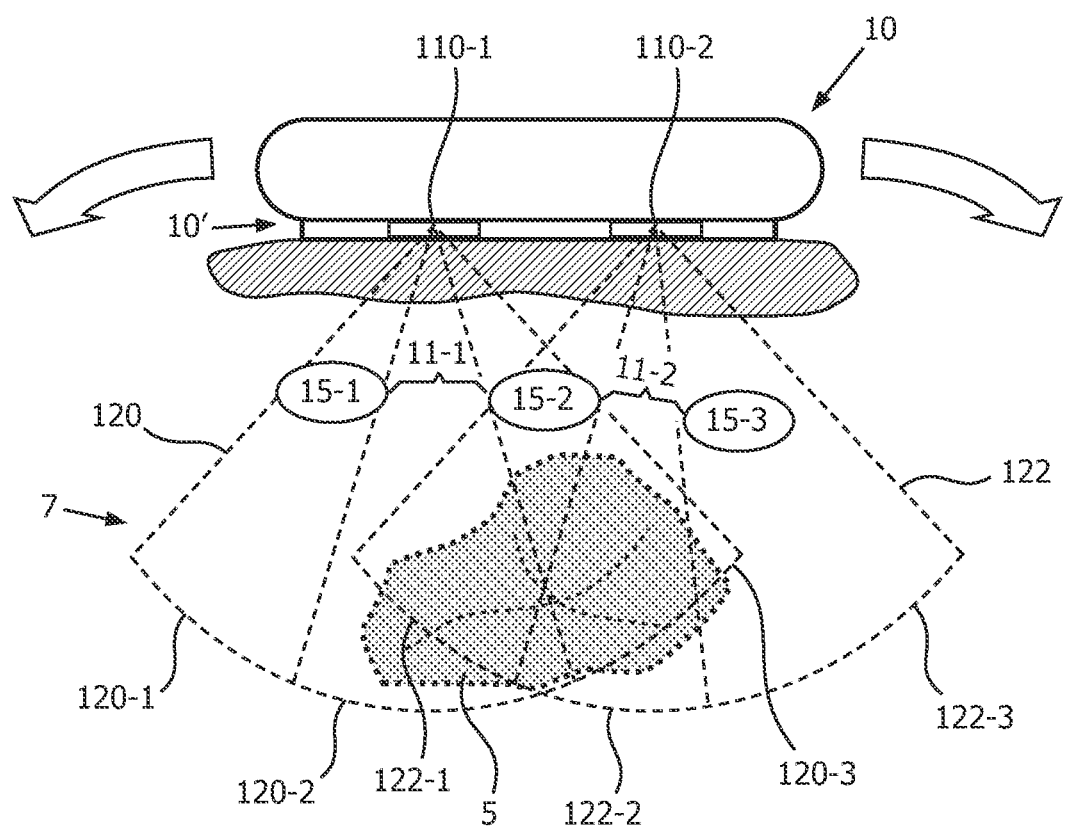
FIG. 1 illustrates intercostal gaps in an acoustic image aperture which might be produced by the presence of ribs between an acoustic transducer and at least a portion of an imaging region.

FIG. 1 illustrates intercostal gaps in an acoustic image aperture which might be produced by the presence of obstructions (e.g., ribs) disposed between an acoustic transducer and at least a portion of an imaging region.

In particular FIG. 1 illustrates an acoustic probe 10 (e.g., an ultrasound probe), including an acoustic transducer array 10' for imaging an imaging region 7, which includes a region of interest (ROI) 5, for example a heart. Imaging region 7 also includes a plurality of obstructions 15-1, 15-2, 15-3, for example ribs, which are separated and spaced apart from each other by intercostal spaces 11-1 and 11-2. In general, acoustic probe 10 and acoustic transducer array 10' may be components of an acoustic imaging apparatus (e.g., an ultrasound imaging system). Acoustic transducer array 10' includes a plurality of acoustic elements (e.g., ultrasound elements). The acoustic elements of acoustic transducer array 10' may be configured to perform a transmit operation by receiving an electrical signal, for example from a microbeamformer of the acoustic imaging apparatus, and in response thereto transmitting a corresponding acoustic signal to imaging region 7. The acoustic elements of acoustic transducer array 10' may also be configured to perform a receive operation by receiving an acoustic signal (e.g., an acoustic echo) from imaging region 7 and in response thereto, supplying a corresponding electrical signal to signal processing circuits of the acoustic imaging apparatus. Further details of example embodiments of acoustic probe 10, acoustic transducer array 10' and an acoustic imaging apparatus which includes acoustic probe 10 and acoustic transducer array 10', will be provided below with respect to the description of FIG. 3.

In operation, apertures 110-1 and 110-2 are formed by acoustic transducer array 10' form corresponding sector scans 120 and 122 of imaging region 7, and particularly ROI 5. As can be seen in FIG. 1, in this example, obstructions 15-1, 15-2, 15-3 are disposed between acoustic transducer array 10' and ROI 5. Accordingly, scan 120 includes a first portion 120-1 which is blocked or shadowed by obstruction 15-1, a second portion 120-2 which passes through intercostal space 11-1 and comprises the field of view of aperture 110-1, and a third portion 120-3 which is blocked or shadowed by obstruction 15-2. Similarly, scan 122 includes a first portion 122-1 which is blocked or shadowed by obstruction 15-2, a second portion 122-2 which passes through intercostal space 11-2 and comprises the field of view of aperture 110-2, and a third portion 122-3 which is blocked or shadowed by obstruction 15-3.

The acoustic imaging apparatus employs beamforming to reconstruct an image of imaging region 7. The quality of the image is related to the point-spread function (PSF), or response of the acoustic imaging apparatus to a single point. The PSF is related to the aperture(s) 110-1, 110-2, etc. of the acoustic transducer array 10'. In the far field approximation, the lateral profile of the PSF is the square of the Fourier transform of the aperture amplitude distribution. If no apodization is applied to the aperture(s), the PSF would be a $sinc^2$ function. However, as illustrated in FIG. 1, part of the aperture(s) is blocked by one or several obstacles. If the blocked part of the aperture is along the edge of the aperture, this will result in a loss of resolution. If it is within the aperture, it will result in grating lobes that may severely reduce the image quality. The same phenomenon results from a gap in the aperture, which can be caused by non-functioning elements, or if one attempts to image coherently with two probes that are separated by a gap.

Figure 2:
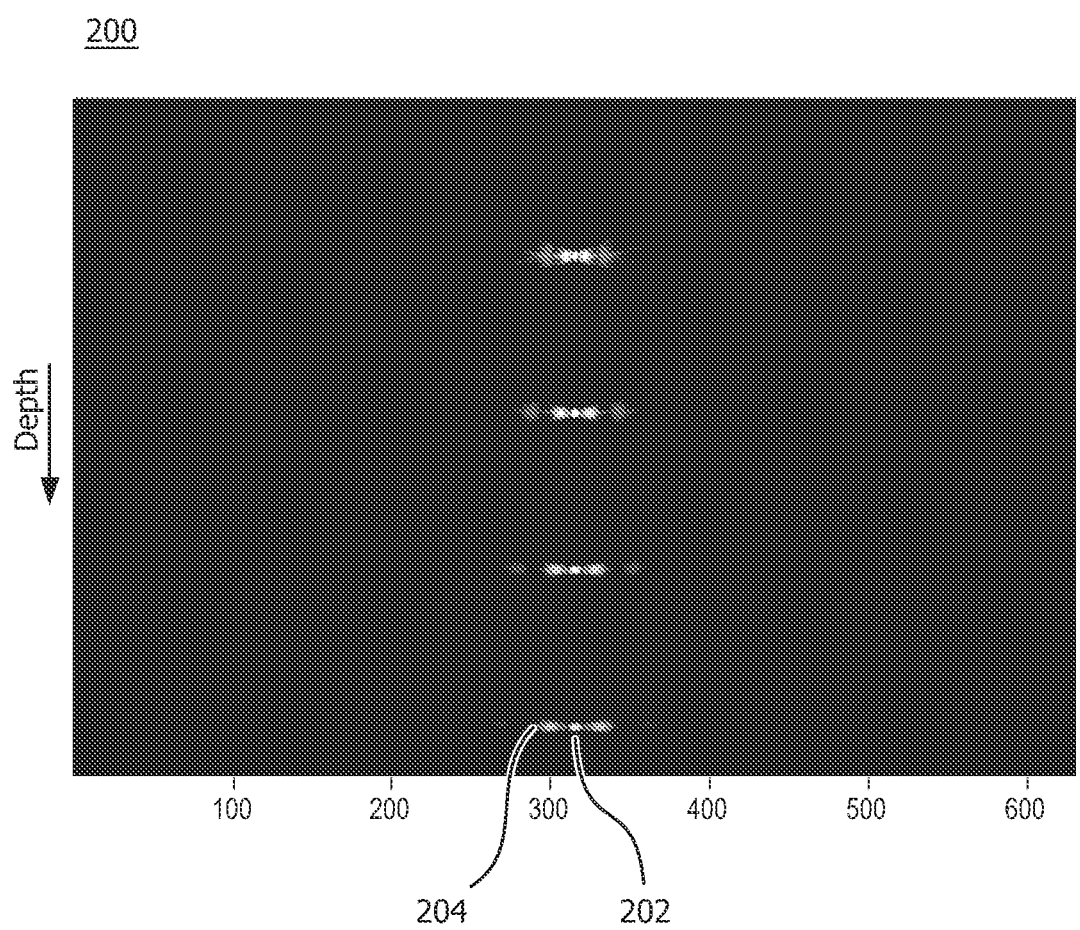
FIG. 2 illustrates strong grating lobes are observed on either side of the main lobe in an acoustic image produced in a situation such as that illustrated in FIG. 1.

FIG. 2 illustrates that strong grating lobes 204 are observed on either side of the main lobe 202 in an acoustic image 200 produced by acoustic probe 10 in a situation such as that illustrated in FIG. 1 and described above where obstructions block imaging of one or more portions of the imaging region by one or more apertures. In particular, FIG. 2 depicts a simulated PSF when a 200-element aperture was divided into three 42-elements sub-apertures, separated by two 37-elements gaps (in this case simulated by inactive elements). The points of the simulated phantoms are at 4, 8, 12, and 16 cm depths with increasing depth from top to bottom of the image.

The present inventors have discovered and appreciated that when a gap or blockage separates a large aperture into several sub-apertures, the resolution of the full, non-blocked aperture, can be restored by using a compensation algorithm, as long as the gaps are smaller than the sub-apertures. In various embodiments described below, compensation algorithms exploit redundancy of the round-trip signal. In particular, various embodiments described below are based on the concept of redundancy of the round-trip ultrasound signal [1]: Let $N_{Tx}$ and $N_{Rx}$ be the index of the transmitting and respective receiving element in an acoustic transducer array. In the far-field (and in absence of phase aberration), the signals for all pairs of Tx/Rx elements such that the sum $N_{Tx}+N_{Rx}$ is constant are identical. Therefore if some of the pairs are missing because they are blocked by ribs, they can be replaced by identical pairs that are not blocked.

Figure 3:
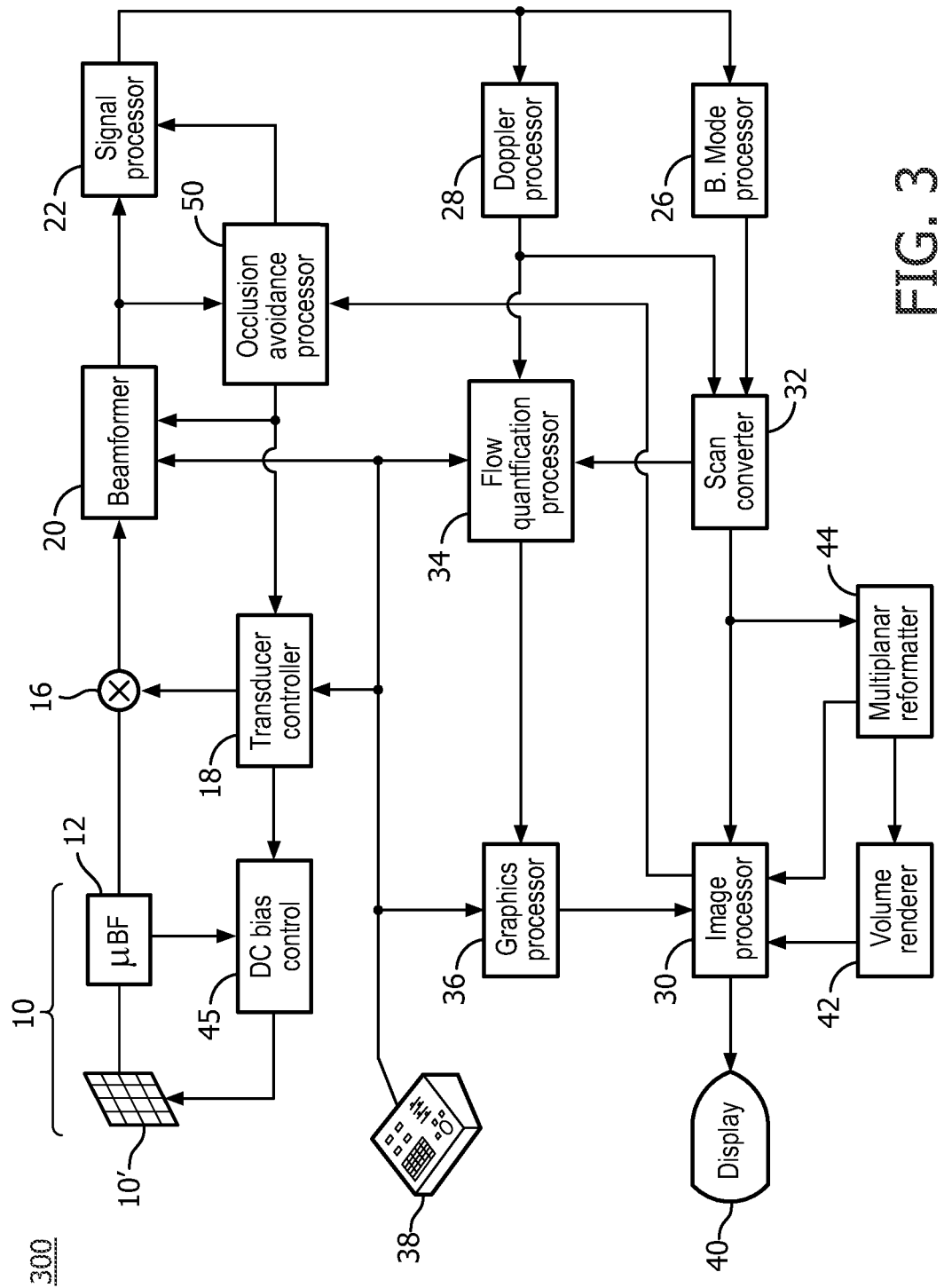
FIG. 3 illustrates one embodiment of an acoustic imaging apparatus.

FIG. 3 illustrates one embodiment of an acoustic imaging apparatus 300 which may implement one or more compensation methods or algorithms for exploiting redundancy of the round-trip ultrasound signal to compensate for gap and blockage of the transducer array aperture(s). In acoustic imaging apparatus 300, an acoustic transducer array 10' (e.g., a capacitive micromachined ultrasonic transducer (CMUT) array) is provided in an acoustic probe 10 for transmitting ultrasonic waves and receiving echo information. The transducer array 10' may alternatively comprise piezoelectric transducer elements formed of materials such as PZT or PVDF. The transducer array 10' is a one- or a two-dimensional array of transducer elements capable of scanning in a 2D plane and/or in three dimensions for 3D imaging. The transducer array 10' is coupled to a microbeamformer 12 in the acoustic probe 10 which controls transmission and reception of signals by the CMUT array cells or piezoelectric elements. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer 12 is coupled by the probe cable to a transmit/receive (T/R) switch 16 which switches between transmission and reception and protects the main beamformer 20 from high energy transmit signals when a microbeamformer 12 is not used and the transducer array 10' is operated directly by the main system beamformer 20. The transmission of ultrasonic beams from the transducer array 10 under control of the microbeamformer 12 is directed by a transducer controller 18 coupled to the microbeamformer by the T/R switch and the main system beamformer 20, which receives input from the user's operation of the user interface or control panel 38. One of the functions controlled by the transducer controller 18 is the direction in which beams are steered and focused. Beams may be steered straight ahead from (orthogonal to) the transducer array 10', or at different angles for a wider field of view. The transducer controller 18 can be coupled to control a DC bias control 45 for the CMUT array. The DC bias control 45 sets DC bias voltage(s) that are applied to the CMUT cells.

The partially beamformed signals produced by the microbeamformer 12 on receive are coupled to a main beamformer 20 where partially beamformed signals from individual patches of transducer elements are combined into a fully beamformed signal. For example, the main beamformer 20 may have 128 channels, each of which receives a partially beamformed signal from a patch of CMUT transducer cells or piezoelectric elements. In some embodiments, each patch may comprise dozens or hundreds of CMUT transducer cells or piezoelectric elements. In this way the signals received by a large number transducer elements (e.g., dozens, hundred, or thousands of elements) of a transducer array 10' can contribute efficiently to a single beamformed signal.

The beamformed signals are coupled to a signal processor 22. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles. The signal processor may also perform additional signal enhancement such as speckle reduction, signal compounding, and noise elimination. The bandpass filter in the signal processor can be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals are coupled to a B mode processor 26 and a Doppler processor 28. The B mode processor 26 employs detection of an amplitude of the received acoustic signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.) The Doppler processor 28 processes temporally distinct signals from tissue movement and blood flow for the detection of the motion of substances such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material. This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B mode and Doppler processors are coupled to a scan converter 32 and a multiplanar reformatter 44. The scan converter arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field with their Doppler-estimated velocities to produce a color Doppler image which depicts the motion of tissue and blood flow in the image field. The multiplanar reformatter will convert echoes which are received from points in a common plane in a volumetric region of the body into an ultrasonic image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.) The 2D or 3D images are coupled from the scan converter 32, multiplanar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made. Output data from the quantification processor is coupled to a graphics processor 36 for the reproduction of measurement graphics and values with the image on the display 40. The graphics processor 36 can also generate graphic overlays for display with the acoustic images. These graphic overlays can contain standard identifying information such as patient name, date and time of the image, imaging parameters, and the like. For these purposes the graphics processor receives input from the user interface 38, such as patient name. The user interface is also coupled to the transmit controller 18 to control the generation of acoustic signals from the transducer array 10' and hence the images produced by the transducer array and the acoustic system. The user interface is also coupled to the multiplanar reformatter 44 for selection and control of the planes of multiple multiplanar reformatted (MPR) images which may be used to perform quantified measures in the image field of the MPR images.

Acoustic imaging apparatus 300 also includes an occlusion avoidance processor 50 which may cooperate with transducer controller 18, beamformer 20, signal processor 22, and image processor 30 to exploit redundancy in transmit/receive pair paths among the acoustic transducers in acoustic transducer array 10' to compensate for missing image data of the imaging region due to the one or more obstructions; and to produce an image of the imaging region from the compensated image data. Example embodiments of such operations by occlusion avoidance processor 50 will be described in greater detail below.

Figure 4:
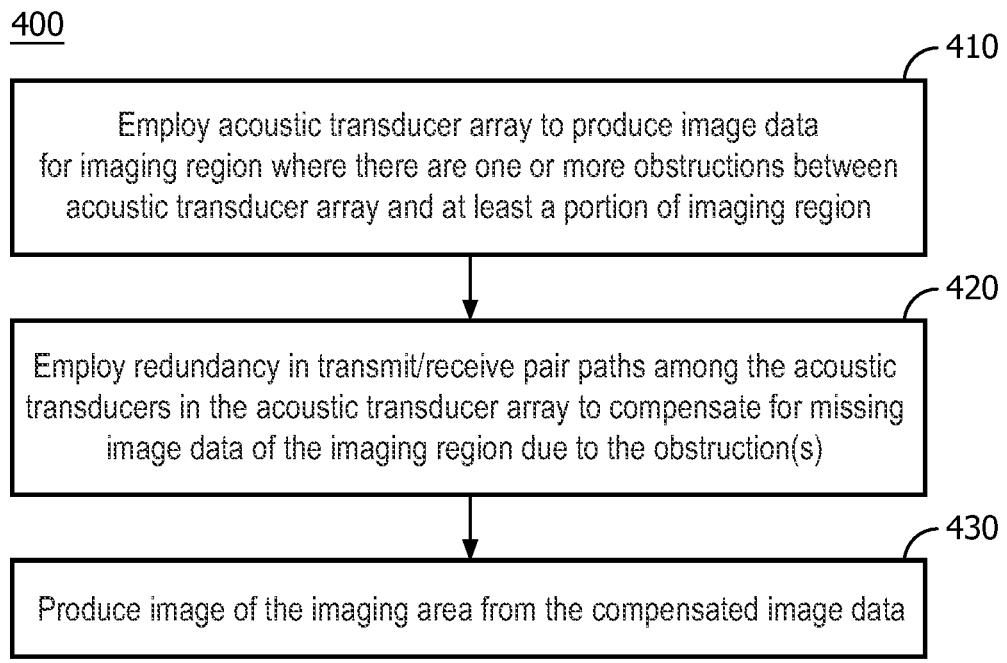
FIG. 4 is a flowchart illustrating one embodiment of a method 400 of imaging an imaging region when there are one or more obstructions between the imaging device and at least a portion of the imaging region.

FIG. 4 is a flowchart illustrating one embodiment of a method of imaging an imaging region when there are one or more obstructions between the imaging device and at least a portion of the imaging region.

In an operation 410, an acoustic transducer array is employed to produce image data for an imaging region where there are one or more obstructions between the acoustic transducer array and at least a portion of the imaging region.

In an operation 420, redundancy in transmit/receive pair paths among the acoustic transducers in the acoustic transducer array is exploited to compensate for missing image data of the imaging region due to the one or more obstruction(s).

In an operation 430, an image of the imaging area is produced from the compensated image data.

Redundancy is particularly clear in the far-field, where the Fraunhoffer approximation holds. In that case, the field and the amplitude distribution in the aperture are related by a simple Fourier transform. For example, in the far-field, the field generated by a single element will be a plane wave. Let $I_{Tx}$ and $I_{Rx}$ be the indexes of the transmitting and receiving elements. In the far-field, the corresponding fields will be $\exp(j.k.x(I_{Tx}))(resp.\exp(j.k.x(IRx))$ where k is the wave number and $x(I_{Tx})$ is the physical coordinate of the transmitting element in the array. The round-trip field is the product of the transmit and receive fields, and is expressed as $\exp(j.k.(x(ITx)+x(I_{Rx})))$. Thus all pair of elements with identical $x(I_{Tx})+x(I_{Rx})$ will generate the same round-trip field. These pairs of elements are said to be redundant.

The angular spectrum of a field is its decomposition into its lateral spatial frequencies. Here, the term "angular spectrum" is used in reference to the lateral spatial spectrum of the PSF. It is expressed as the Fourier transform of the lateral profile of the PSF. In the far field, the one-way (transmit or receive only) angular spectrum is proportional to the aperture amplitude distribution, according to the Fraunhoffer approximation as discussed above. If the active aperture is a rectangle, the one way PSF is a sinc function. The round trip point spread function is a $sinc^2$ function, and the angular spectrum for the round trip PSF is a triangle function. The round trip angular spectrum can also be computed as the convolution product of the transmit and receive aperture's amplitude distributions.

Figure 5:
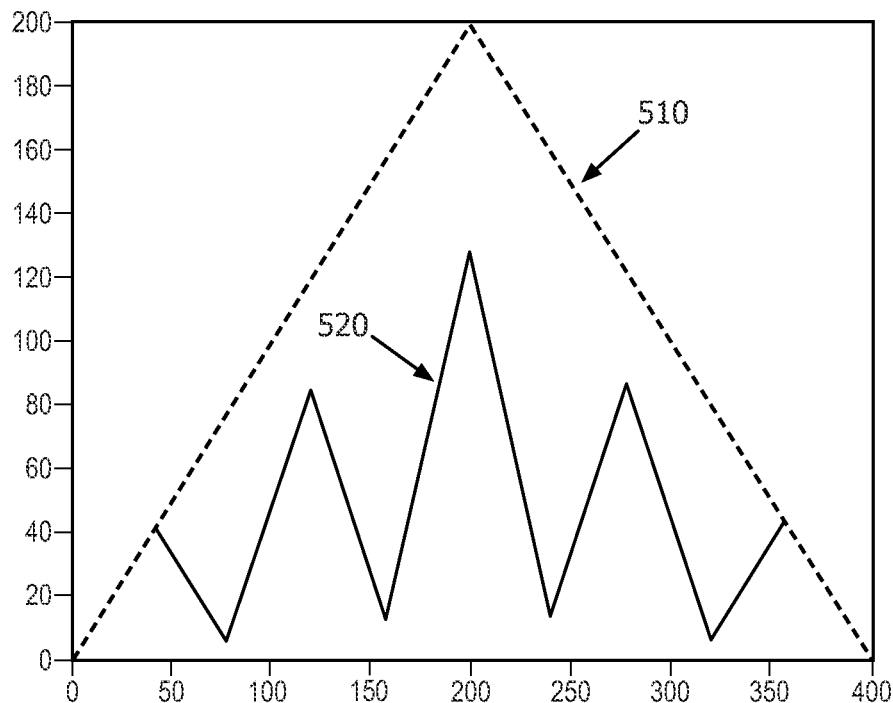
FIG. 5 illustrates examples of: (1) an ideal angular spectrum for an acoustic transducer array with respect to an imaging region which would exist in the absence of the one or more obstructions; and (2) an angular spectrum for the acoustic transducer array with respect to the imaging region in the presence of the one or more obstructions.

FIG. 5 illustrates examples of: (1) an ideal angular spectrum 510 (dashed lines) for a rectangular acoustic transducer array having 200 elements with respect to an imaging region which would exist in the absence of the one or more obstructions; and (2) an angular spectrum 520 (solid lines) for the same acoustic transducer array with respect to the imaging region in the presence of one or more obstructions.

It can be seen from FIG. 5 that, as long as the obstructions (e.g., ribs 15) are not larger than the intercostal spaces, the amplitude for each frequency is non-zero. Therefore, the true angular spectrum (and point spread function) can be recovered by adding more weight to the angular frequencies that are less represented due to the presence of the obstructions (e.g., ribs 15). The weight for each frequency in the angular spectrum is the ratio of the ideal amplitude in the absence of the obstructions (the value of spectrum 510 at that frequency) divided by the actual amplitude (the value of spectrum 520 at that point) dues to the presence of the obstructions. The collection of these weights or coefficients across all of the angular frequencies of the acoustic transducer array is referred to here as an inverse filter.

One straightforward way to implement the method is with a synthetic aperture acquisition. Once the position(s) of the obstruction(s) (e.g., ribs 15) is known angular spectrum 520 can be computed for the acoustic transducer array with respect to the imaging region in the presence of the one or more obstructions (e.g., ribs 15), and the weights or coefficients for each transmit/receive pair of elements can be obtained by taking the ratio of angular spectrum 520 and ideal angular spectrum 510. Here, the position(s) or location(s) of the obstruction(s) may be determined by a variety of techniques, including, for example using a rib detection algorithm which may employ an image of imaging area 7 produced by acoustic imaging apparatus 300 together with a feature recognition algorithm. U.S. provisional patent application 61/913,576, filed on 9 Dec. 2013, discloses embodiments of rib detection algorithms. The contents of U.S. provisional patent application 61/913,576 are hereby incorporated herein by reference. Other methods could be employed, including using image data obtained from other imaging modalities, including X-ray data, magnetic resonance imaging (MM) data, etc.) However, whatever method of locating the position(s) of the obstruction(s) (e.g., ribs 15) is employed, once the location(s) are determined angular spectrum 520 can be computed for the acoustic transducer array with respect to the imaging region in the presence of the one or more obstructions (e.g., ribs 15), and the weights or coefficients for each transmit/receive pair of elements can be obtained by taking the ratio of angular spectrum 520 and ideal angular spectrum 510, as mentioned above. During the synthetic aperture summation, each TX/RX element pair is weighted with the corresponding weight coefficient. One disadvantage of this method may be low signal-to-noise ratio (SNR) due to the use of single element transmits.

Figure 6:
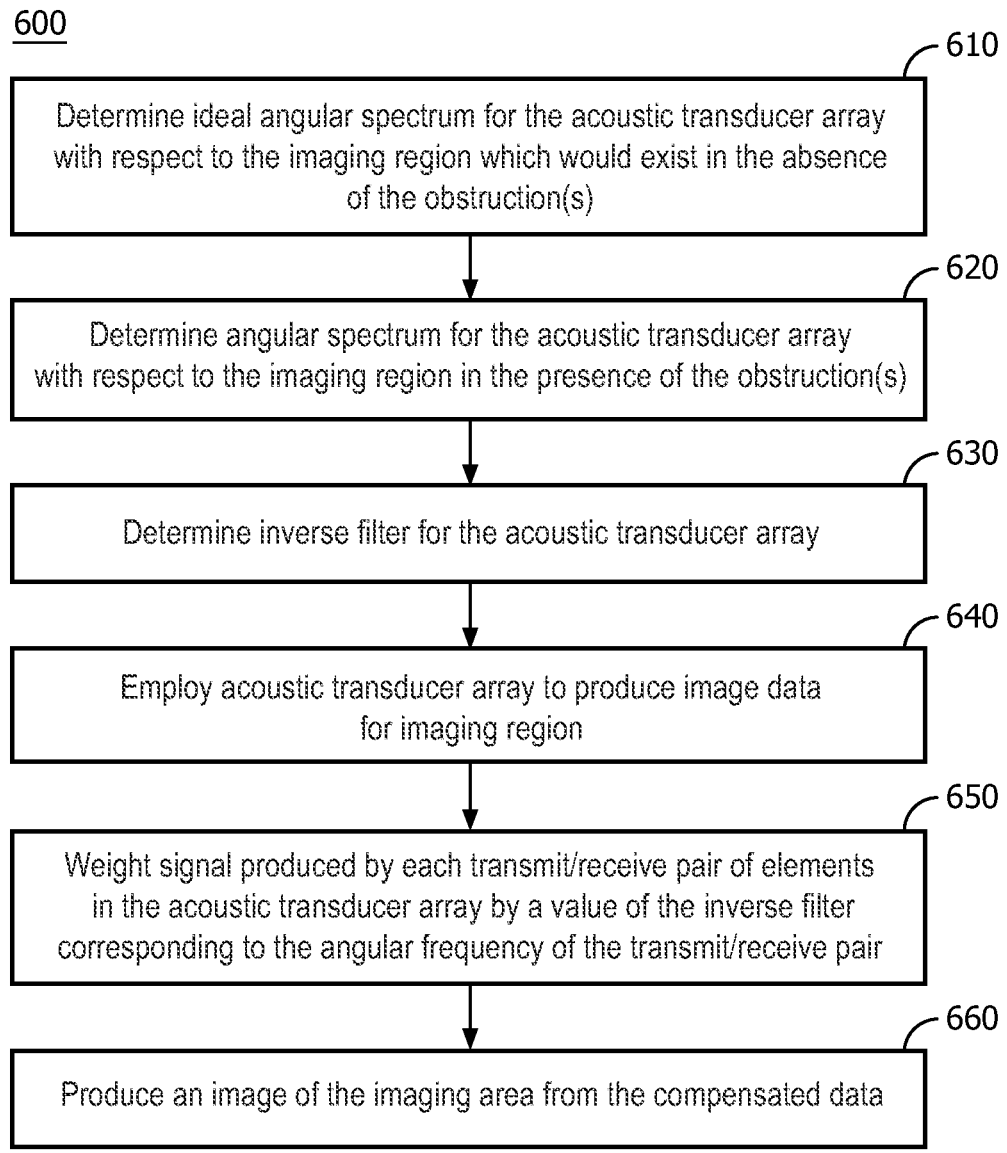
FIG. 6 is a flowchart illustrating another embodiment of a method of imaging an imaging region when there are one or more obstructions between the imaging device and at least a portion of the imaging region.

FIG. 6 is a flowchart illustrating an embodiment of a method 600 of imaging an imaging region when there are one or more obstructions (e.g., ribs 15) between the imaging device and at least a portion of the imaging region. It should be understand that various operations of method 600 may be performed in a different order than that illustrated in FIG. 6 and described below.

In an operation 610, the ideal angular spectrum is determined for the acoustic transducer array with respect to the imaging region which would exist in the absence of the obstruction(s).

In an operation 620, the angular spectrum is determined for the acoustic transducer array with respect to the imaging region in the presence of the obstruction(s).

In an operation 630, an inverse filter is determined for the acoustic transducer array.

In some embodiments, the inverse filter may be obtained by dividing an ideal angular spectrum for the acoustic transducer array with respect to the imaging region which would exist in the absence of the one or more obstructions (e.g., 510 in FIG. 5), by an angular spectrum for the acoustic transducer array with respect to the imaging region in the presence of the one or more obstructions (e.g., 520 in FIG. 5), which may be determined as explained above.

In an operation 640, the acoustic transducer array is employed to produce image data for imaging region 7.

In an operation 650, the signal produced by each transmit/receive pair of elements in the acoustic transducer array in the imaging operation is weighted by a value of the inverse filter corresponding to the angular frequency of the transmit/receive pair.

In an operation 660, an image of the imaging area is produced from the compensated image data.

The description above simplifies the effect of the obstructions, modeling them as if they are thin, screen-like features located immediately in front of the acoustic transducer array. In reality, the obstructions (e.g., ribs 15) are typically thick and are disposed at a distance from the acoustic transducer array. Consequently, the "shadow" of the obstructions on the aperture will change with the position of the imaging point. Thus the effective Tx and Rx aperture, as well as the angular spectrum, changes for each point in the imaging region. However, if the location(s) of the obstruction(s) are determined, a ray tracing algorithm can be used to compute the aperture "seen" by each point, the angular spectrum for each point can be computed, and the algorithm described above can be used.

Accordingly, in some embodiments of the method 600 described above, determining the inverse filter for the acoustic transducer array, weighting the signal produced by each transmit/receive pair of elements in the acoustic transducer array by the value of the inverse filter corresponding to the angular frequency of the transmit/receive pair, and generating the acoustic image by summing the weighted signals of all the transmit/receive pairs, can include performing an algorithm for each of a plurality of points of interest in the imaging region. The algorithm can include: determining an inverse filter for the acoustic transducer array with respect to the point, wherein when the inverse filter is multiplied by an angular spectrum for the acoustic transducer array with respect to the point in the presence of the one or more obstructions, it produces an ideal angular spectrum for the acoustic transducer array with respect to the point which would exist in the absence of the one or more obstructions; weighting the signal produced by each transmit/receive pair of elements in the acoustic transducer array from the point by a value of the inverse filter corresponding to the angular frequency of the transmit/receive pair; and determining an intensity of the acoustic image at the point by summing the weighted signals produced by each transmit/receive pair of elements in the acoustic transducer array from the point.

In some embodiments, the inverse filter for the acoustic transducer array with respect to each point can be determined by employing a ray tracing algorithm to compute an effective aperture seen by the point.

Figure 7:
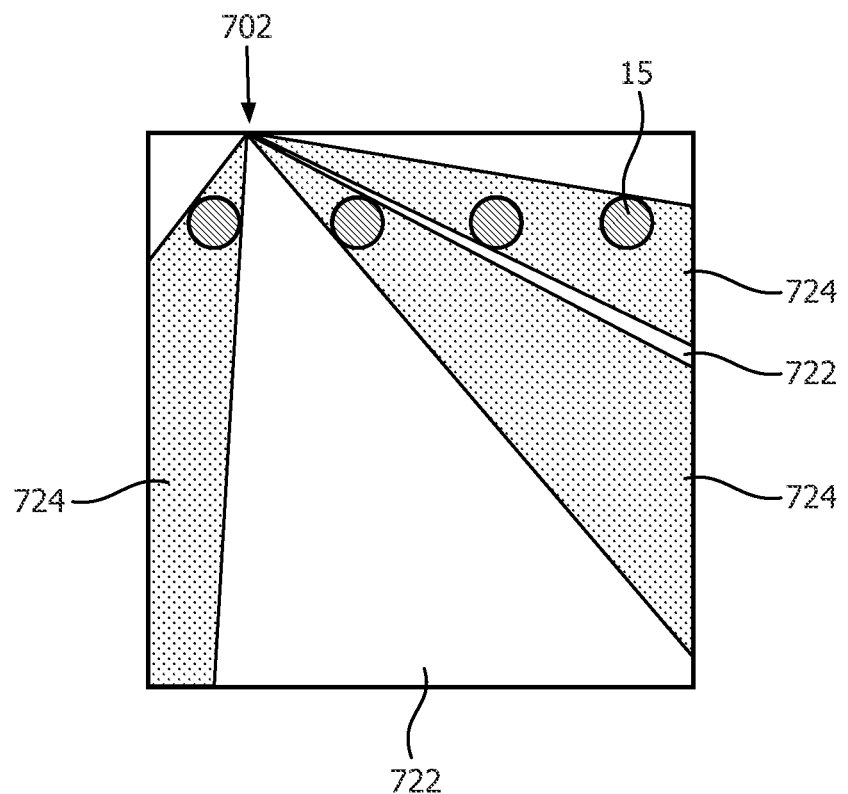
FIG. 7 shows a rib model, illustrating how a ray tracing algorithm may be used to detect which image point sees which transducer element in a transducer array.

FIG. 7 shows a rib model, illustrating how a ray tracing algorithm may be used to detect which image point sees which transducer element in a transducer array in the method 600 of FIG. 6 in the presence of obstructions 15. In particular, FIG. 7 illustrates first areas 722 which can be seen by a particular element 702, and second areas 724 whose view from element 702 are blocked by obstructions 15.

One solution to mitigate the low SNR of the synthetic aperture imaging employed in method 600, while retaining its flexibility, is to use a virtual transducer approach. In such an approach, a set of focused transmit and receive pairs are created. Each focused beam can be seen as a virtual transducer (but with more intensity than a single element) located at the focus of the beam, and the synthetic aperture algorithm can be applied with the array of virtual transducers. An ideal depth for the virtual transducer would be the depth of the obstructions (e.g., ribs 15).

Accordingly, in some embodiments of the method 600 described above, determining the inverse filter for the acoustic transducer array, weighting the signal produced by each transmit/receive pair of elements in the acoustic transducer array by the value of the inverse filter corresponding to the angular frequency of the transmit/receive pair, and generating the acoustic image by summing the weighted signals of all the transmit/receive pairs, can include performing an algorithm which employs virtual transducers. In some embodiments, the algorithm may include: creating an array of virtual transducers from the acoustic transducer array; determining an inverse filter for the array of virtual transducers, wherein when the inverse filter is multiplied by an angular spectrum for the array of virtual transducers with respect to the imaging region in the presence of the one or more obstructions, it produces an ideal angular spectrum for the array of virtual transducers with respect to the imaging region which would exist in the absence of the one or more obstructions; weighting a signal produced by each transmit/receive pair of elements in the array of virtual transducers by a value of the inverse filter corresponding to the angular frequency of the transmit/receive pair, and generating an acoustic image by summing the weighted signals of all the transmit receive pairs.

Other embodiments can exploit redundancy in transmit/receive pair paths among the acoustic transducers in the acoustic transducer array, directly in beam space. Such embodiments may employ conventional beamforming, which may increase the SNR compared to the embodiment of FIG. 6, as the energy from several points in space can be focused in one location. In these embodiments, focused transmits are used instead of single elements transmits. For that purpose, the round-trip weights that are calculated must be split into weights for the transmit aperture and weights for the receive aperture. This can be done using a decomposition algorithm, such as a singular value decomposition, an eigenvalue decomposition, or other decomposition. However, the desired round-trip point spread function cannot be achieved with a single transmit-receive operation, it requires a sum of two or more transmit-receive operations (for example, the second transmit/receive point spread function may actually only contain the side lobe and can be subtracted from the first one that contains both main lobe and side lobes).

For example, let W by the matrix of round-trip weights. For example, $W_{ij}$ is the weight corresponding to the pair consisting of the transmit i and receive j given by the value of the angular spectrum for the corresponding Tx/Rx pair.

Let U(resp. V) be the apodization vector in transmit (resp. receive) (each element of U is a weight to apply to an element in the array when transmitting). For a given U and V, W is given by W=UV* where * stands for the matrix transpose.

Here, we are interested in the inverse problem: W is known, but is it always possible to find a set of corresponding transmit and receive aperture? If the rank of W is 1, then W can be decomposed into the product of 1 transmit and 1 receive aperture. However, if the rank of W is larger than 1, as it is the case in the gaps compensation algorithm, W can only be decomposed into a sum of product of several transmit and receive apertures, via a singular value decomposition (SVD):

W=USV*, where S is a diagonal matrix of singular values and U(resp. V) is a matrix whose columns are the various transmit (resp. receive) apodization vectors.

In practice, it has been found that only 2 singular values are significant (the other ones are very small) so that W can be in a very good approximation expressed as the sum of two transmit-receive beams $$W = S(1,1) \cdot U_1 \cdot V_1 + S(2,2) \cdot U_2 V_2 \tag{1}$$

Due to the symmetry of W, transmit and receive apodizations are identical: $U_1 = V_1$.

Figure 8:
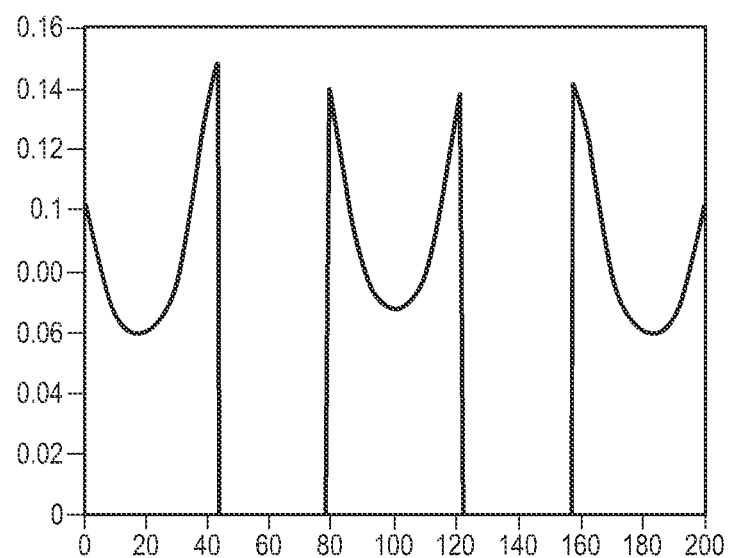
FIG. 8 illustrates apodization functions for two sets of transmit/receive apertures to be employed in two transmit-and-receive operations.
Figure 8:
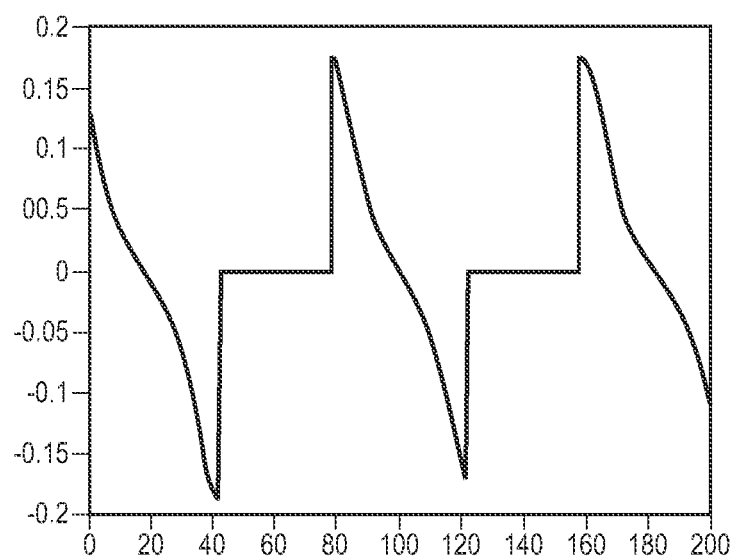

FIG. 8 illustrates apodizations 810 (U1) and 820 (U2) for the simulated aperture described above with respect to FIG. 2. Both apodizations 810 and 820 have strong weights near the edges of the sub-apertures. Apodization 810 alone still generates strong side lobes. However, when point spread functions produced using each of the apodizations 810 and 820 individually are combined according to Equation (1) above, then the grating lobes disappear from the resulting point spread function. In fact, apodization 820 generates a point spread function with no main lobe and only grating lobes that can be subtracted from the first point spread function produced using apodization 810.

In some embodiments, first apodization 810 ($U_1$) may be employed both in transmit and receive operations to generate a first set of image data. Similarly, a second set of image data is generated using second apodization 820 ($U_2$) for transmit and receive operations. The two sets of summed data are then weighted by their respective singular values as shown in Equation 1 and combined to obtain the final image data.

Figure 9:
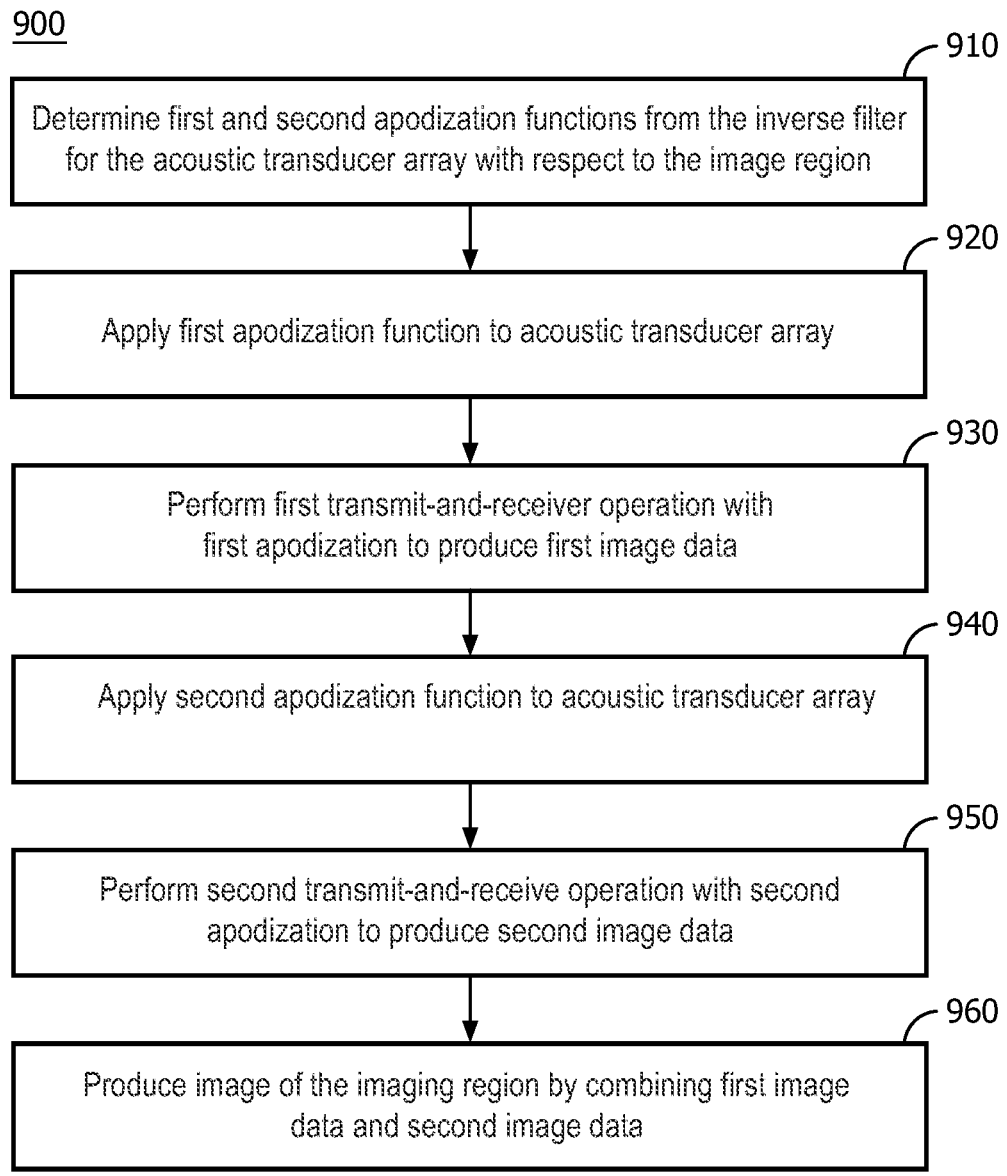
FIG. 9 is a flowchart illustrating yet another embodiment of a method of imaging an imaging region when there are one or more obstructions between the imaging device and at least a portion of the imaging region.

FIG. 9 is a flowchart illustrating an embodiment of a method 900 of imaging an imaging region when there are one or more obstructions (e.g., ribs 15) between the imaging device and at least a portion of the imaging region which can employ conventional beamforming. It should be understand that various operations of method 900 may be performed in a different order than that illustrated in FIG. 9 and described below.

In an operation 910, first and second apodization functions are determined from an inverse filter for the acoustic transducer array with respect to the imaging region.

FIG. 8 illustrate example first and second apodization functions 810 and 820 for two sets of transmit/receive apertures which may be employed in the method 900 of FIG. 9.

In an operation 920, the first apodization function is applied to the acoustic transducer array.

In an operation 930, a first transmit-and-receive operation is performed with the first apodization to produce first image data.

In an operation 940, a second apodization function is applied to the acoustic transducer array.

In an operation 950, a second transmit-and-receive operation is performed with the second apodization to produce second image data.

In an operation 960, an image of the imaging region is produced by combining the first image data and the second image data.

Other embodiments of methods which exploit redundancy in transmit/receive pair paths among the acoustic transducers in the acoustic transducer array may employ image based deconvolution. As mentioned above, in the far field, the Fourier transform of a point spread function at a given frequency, is proportional to the aperture. For broadband signals, one can take the 2D spatial Fourier transform of a point spread function, known as k-space. The spectrum at a given wave number k is a scaled version of the round trip angular spectrum derived as described above. The scaling factor is the wave number k itself. This can be derived from the Fraunhoffer approximation: as seen in above, one element of the aperture is associated with a plane wave exp $(j.k.x(I_{Tx}))$. The spatial frequency is proportional to k.

Therefore the inverse filter can be implemented directly in k-space, rather than on the synthetic aperture round-trip pairs.

In some embodiments, the k-space of the image is computed by taking the 2D Fourier transform of the summed RF data (before envelope detection). The inverse filter weights are computed as described above, scaled for each value of k, and multiplied with the spectrum. The temporal bandwidth of the signal can be taken into account at this point. Finally, a 2D inverse Fourier transform is computed to obtain the compensated image. Alternatively, as a multiplication in k-space is equivalent to a convolution in the image domain, the deconvolution can be done directly in the image domain. In that case, the 2D Fourier transform of the inverse filter is computed to obtain a kernel that is convolved with the image (summed RF data). The size of the kernel is roughly the size of the point spread function.

It has been observed that the assumptions underlying the use of image based deconvolution are not as robust as the assumptions underlying the use of the synthetic aperture algorithm as described above. Even in the far field, the k-space spectrum varies significantly as a function of the lateral position of the point. However, this can be addressed by employing a space dependent inverse filter. The weights of the filter can be computed through simulation of the point spread functions. The convolution kernel approach is particularly suited for a space dependent filtering as the kernel can be changed as a function of the position.

Figure 10:
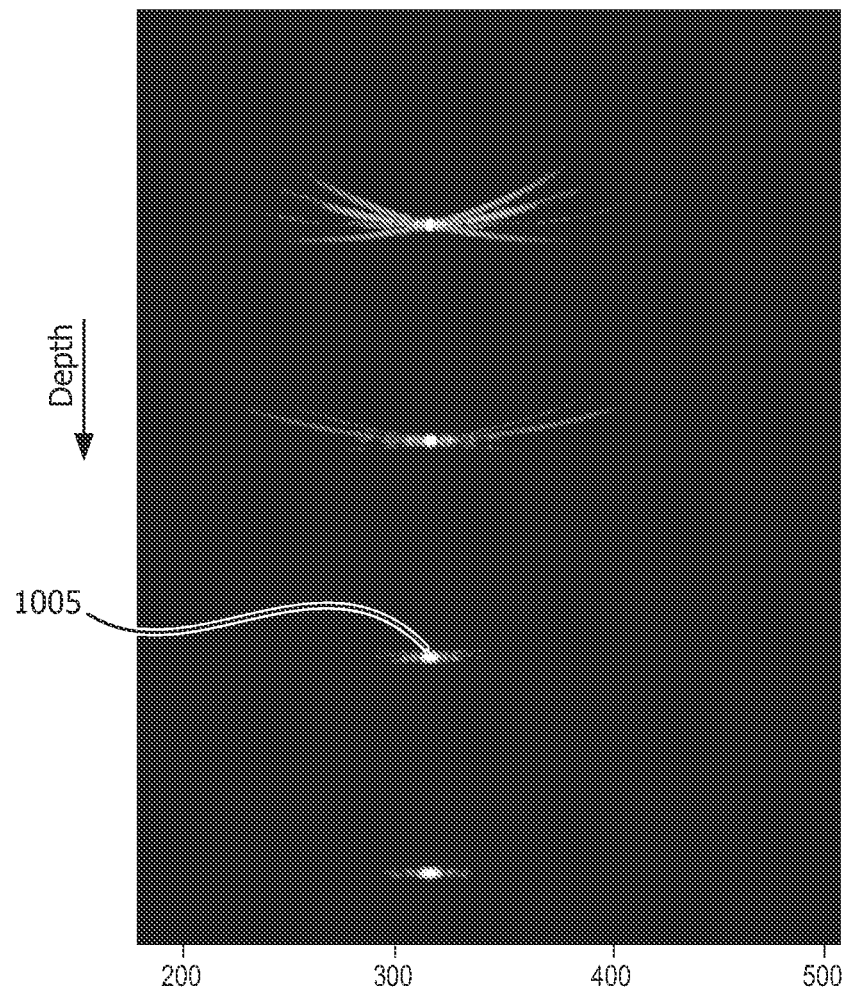
FIG. 10 illustrates a point spread function for the same situation as illustrated in FIG. 2 when a compensation algorithm is employed for the intercostal spaces.

FIG. 10 illustrates a point spread function for the same situation as illustrated in FIG. 2 when a compensation algorithm as described with respect to FIG. 6 is employed for the intercostal spaces. Here, again, the four point scatterers are respectively located at depths of 4, 8, 12 and 16 cm. For the two deepest points at 12 cm and 16 cm, the image is greatly improved compared to FIG. 2. The grating lobes are suppressed and the point spread functions look similar to what would be obtained with the full aperture without any gaps. For the shallowest point at 4 cm, the far field approximation does not hold and the reconstruction is not good. The point at 8 cm is in a transition region.

Figure 11A:
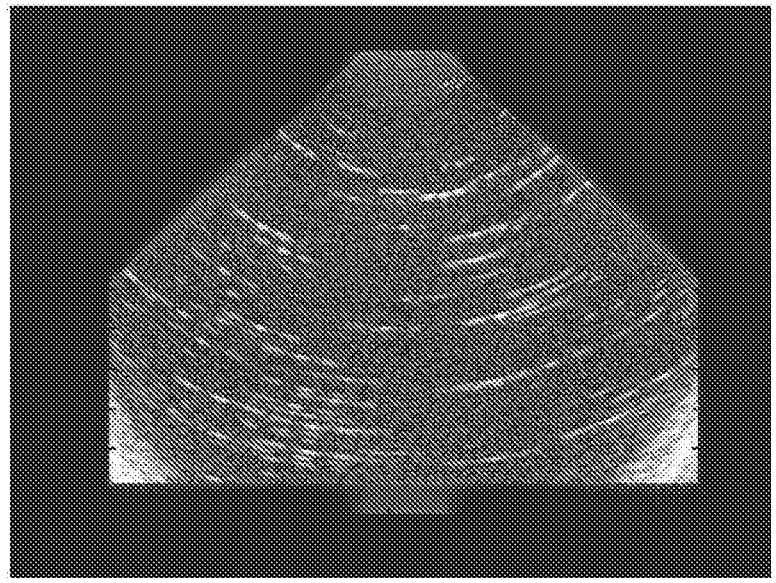
FIGS. 11A and 11B illustrate simulated images with the presence of intercostal gaps in a large aperture, with and without compensation, respectively.
Figure 11B:
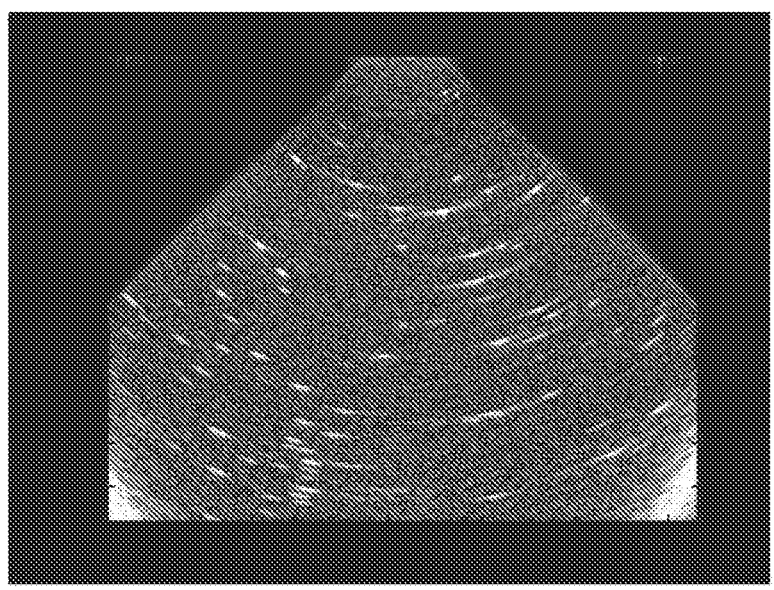

FIGS. 11A and 11B illustrate images which simulate the presence of intercostal gaps in a large aperture, with (FIG. 11B) and without (FIG. 11A) compensation. In particular, one 80-element aperture was used and "mini-ribs" were artificially introduced by blocking some of the elements. Two 13-element blockages were used, leaving three 18-element apertures. It is noted that FIG. 11A shows strong grating lobes, while FIG. 11B shows reduction and in some cases elimination of the grating lobes by employing a gap compensation algorithm as described herein.

FIGS. 12A-D illustrate simulated transthoracic echocardiograms produced using a large aperture when two blockages (e.g., due to two ribs 15) are simulated. As in FIGS. 11A-B, one 80-element aperture is divided into three 18-element apertures separated by two 13-element blockages.

Figure 12A:
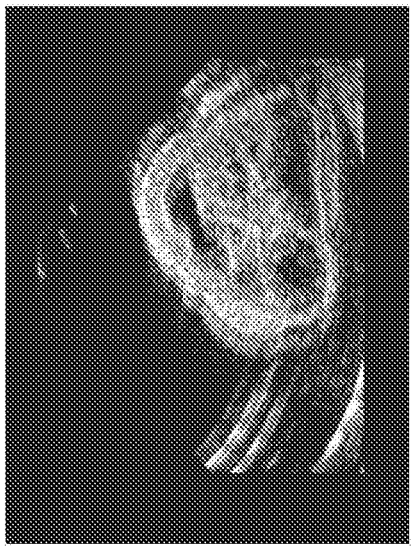
FIG. 12A illustrates a transthoracic echocardiogram produced using a large aperture when two blockages (e.g., due to two ribs) are simulated.

FIG. 12A illustrates a simulated transthoracic echocardiogram produced using a large aperture when two blockages (e.g., due to two ribs) are simulated.

Figure 12B:
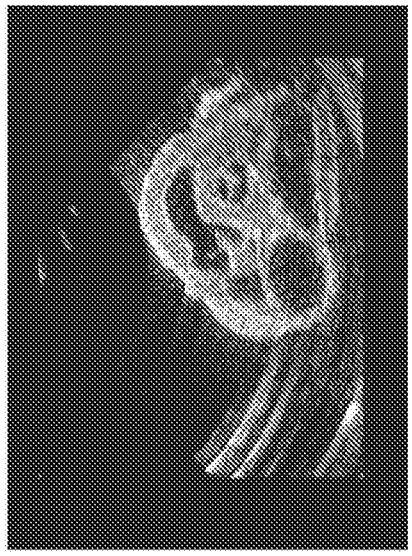
FIG. 12B illustrates a transthoracic echocardiogram produced using a large aperture when two blockages (e.g., due to two ribs) are simulated and an intercostal gap compensation algorithm is employed.

FIG. 12B illustrates a transthoracic echocardiogram produced using a large aperture when two blockages (e.g., due to two ribs) are simulated and an intercostal gap compensation algorithm is employed.

Figure 12C:
FIG. 12C illustrates a reference transthoracic echocardiogram produced using a large aperture similar to FIG. 12A, but when no blockages are present.

FIG. 12C illustrates a reference transthoracic echocardiogram produced using a large aperture similar to FIG. 12A, but when no blockages are present.

Figure 12D:
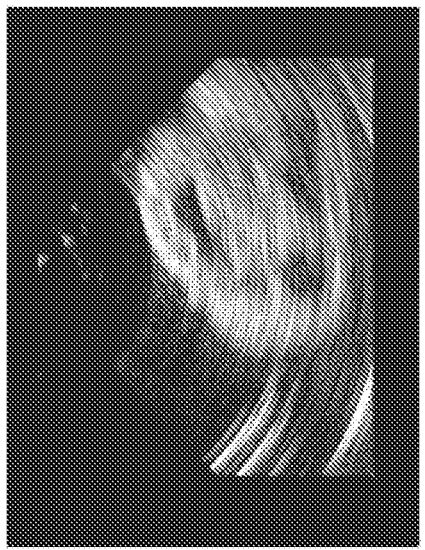
FIG. 12D illustrates a transthoracic echocardiogram produced using a smaller aperture than that used to generate FIGS. 12A-C.

FIG. 12D illustrates a transthoracic echocardiogram produced using a smaller aperture than that used to generate FIGS. 8A-C.

Figure 13:
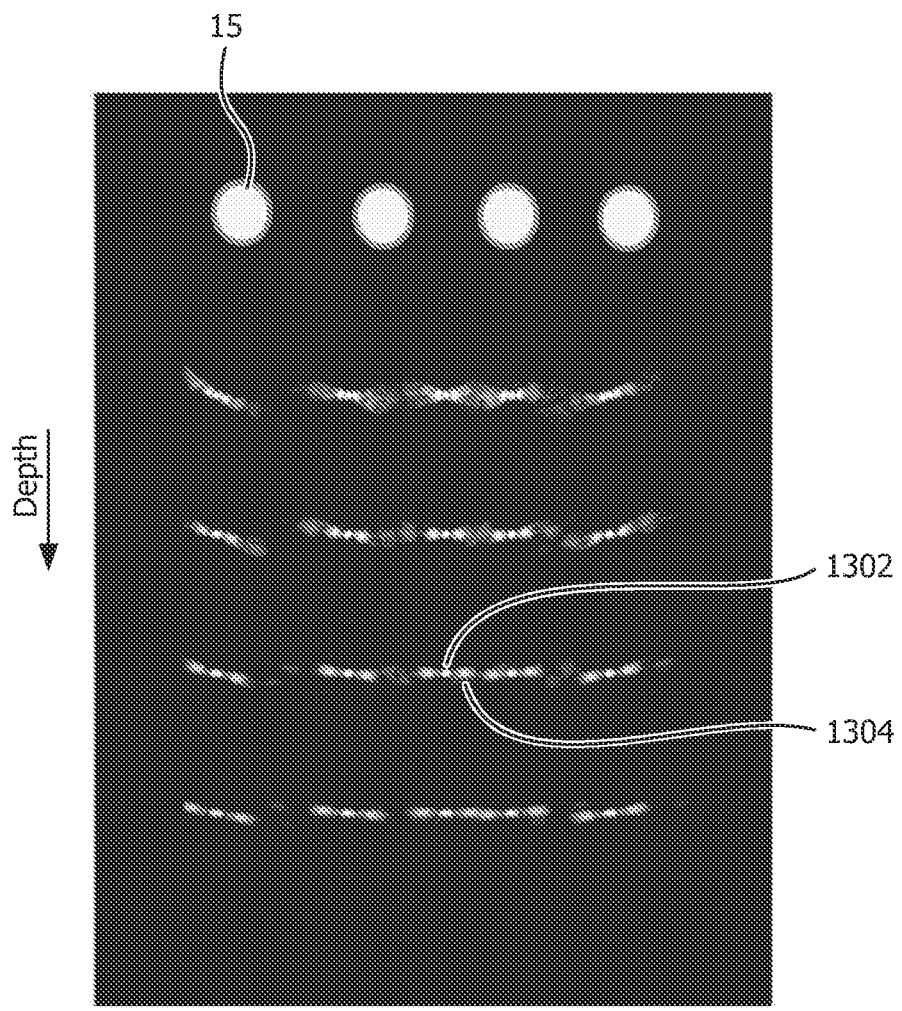
FIG. 13 illustrates a coherent image produced in the presence of ribs.

FIG. 13 illustrates a coherent image produced in the presence of obstructions (e.g., 15). As in FIGS. 2 and 10, four point scatterers are respectively located at depths of 4, 8, 12 and 16 cm. Grating lobes 1304 are shown adjacent to the main lobes 1302.

FIG. 14A illustrates an image produced in the presence of ribs similar to that show in FIG. 13, when coherent compounding using an "intercostal gap compensation" algorithm as described above is employed. FIG. 14B illustrates an image similar to that show in FIGS. 13 and 14A which would be produced in the absence of any obstructions. It can be seen by comparing FIGS. 13, 14A and 14B that for depths greater than 10 cm, the image through the obstructions (e.g., ribs) when the compensation algorithm is employed is nearly as good as if there were no obstructions resent.

Figure 15A:
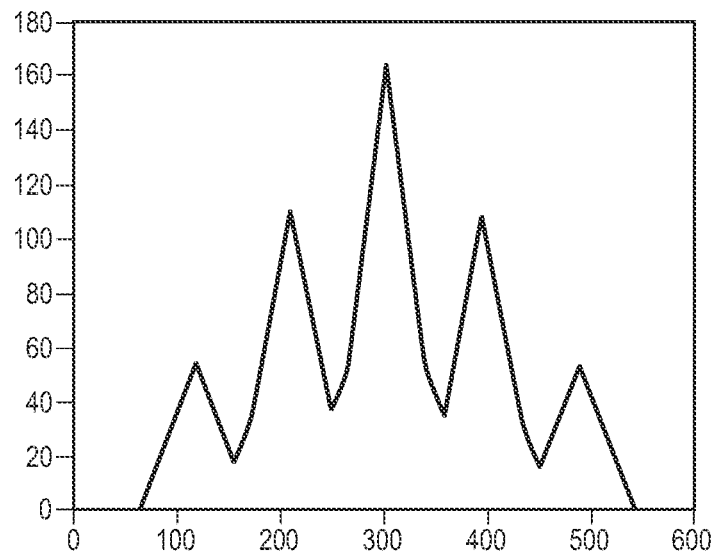
FIG. 15A illustrates the angular spectrum for a point in the far-field center in the model illustrated in FIG. 8.
Figure 15B:
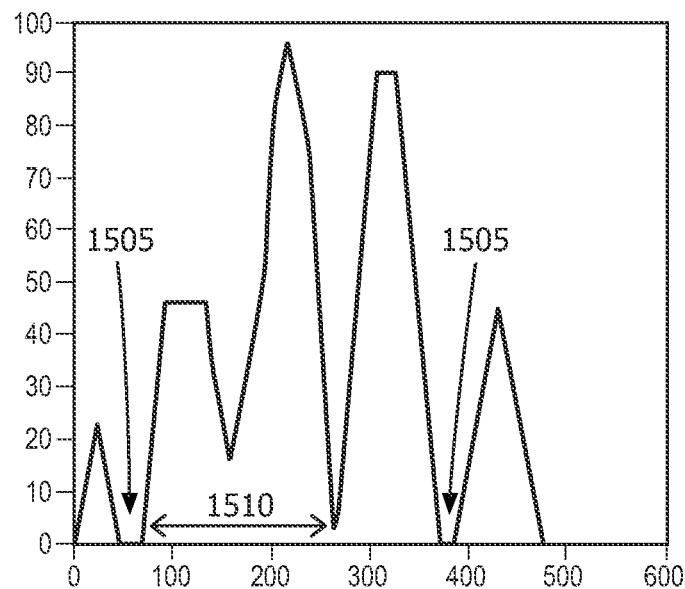
FIG. 15B illustrates the angular spectrum for a point closer to the acoustic transducer array and on the edge of the image in the model illustrated in FIG. 8.
Figure 16:
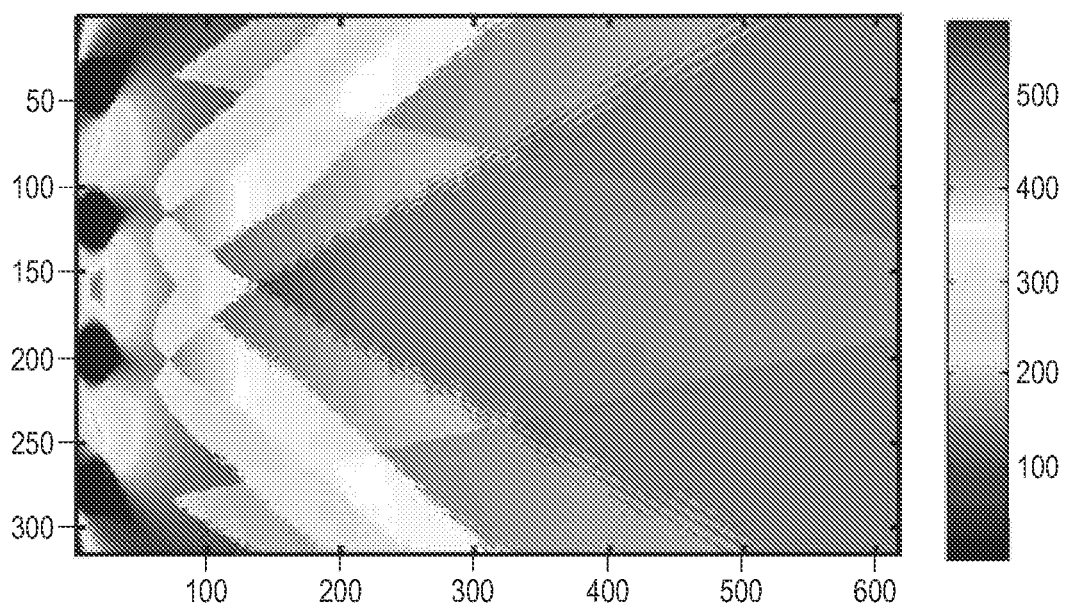
FIG. 16 illustrates for the example of FIG. 8, the maximum round-trip aperture size that could be reconstructed by the algorithm for different points of the image.

FIG. 15A illustrates the angular spectrum for a point in the far-field center in the model illustrated in FIG. 8. FIG. 15B illustrates the angular spectrum for a point closer to the acoustic transducer array and on the edge of the image in the model illustrated in FIG. 8. As shown in FIG. 15B, the angular spectrum has gaps 1505 that cannot be closed by the algorithms described above which exploit redundancy in the TX/RX round trip paths, because the minimum amplitude is zero or is very small. The coherent compounding algorithm could still be used for the part 1510 of the spectrum shown by the arrow. The other part of the spectrum could be added incoherently FIG. 16 illustrates for the example of FIG. 8, the maximum round-trip aperture size that could be reconstructed by the algorithm for different points of the image. The obstructions are disposed along the left edge.

Figure 17:
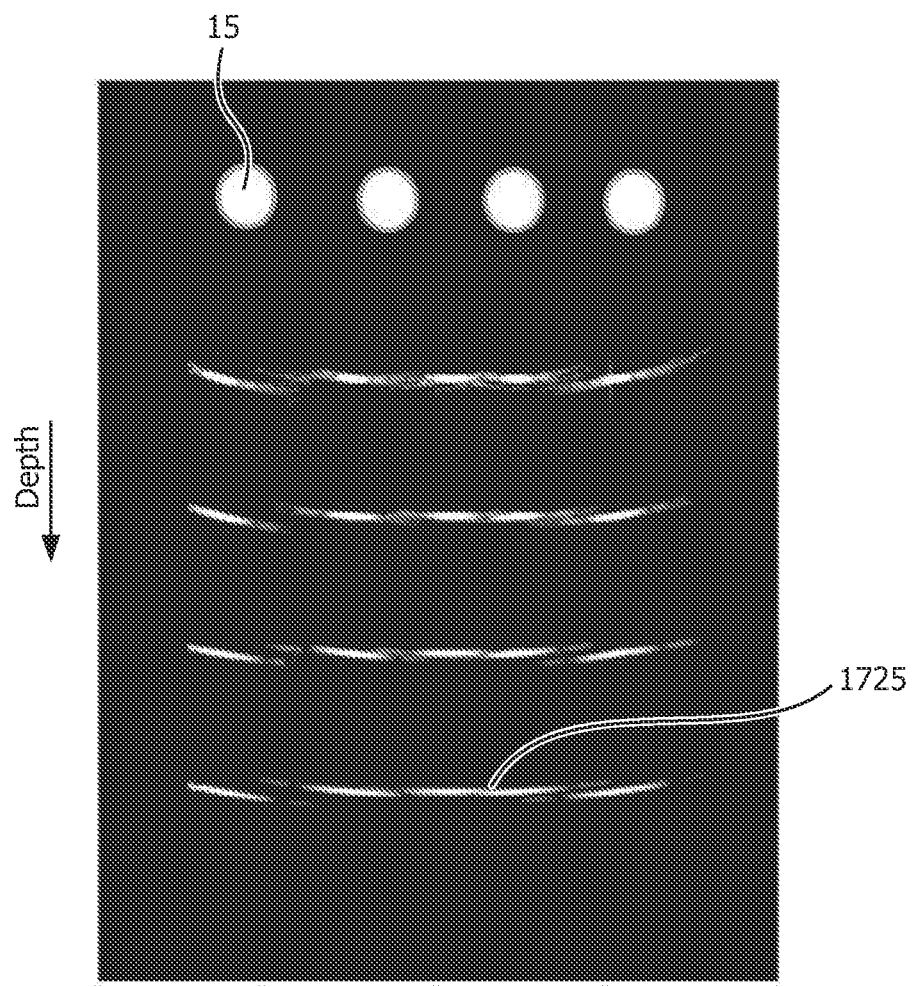
FIG. 17 illustrates the results of a compensation algorithm when the ribs are as large as the intercostal spaces.

FIG. 17 illustrates the results of a compensation algorithm when the obstructions (e.g., ribs) are as large as the intercostal spaces. Here only one intercostal space is used for each point, as the gaps cannot be closed. Incoherent compounding could be employed to improve the results.

While preferred embodiments are disclosed in detail herein, many variations are possible which remain within the concept and scope of the invention. Such variations would become clear to one of ordinary skill in the art after inspection of the specification, drawings and claims herein. The invention therefore is not to be restricted except within the scope of the appended claims.

What is claimed is:

1. A method of imaging an imaging region, the method comprising:
    employing an acoustic transducer array to transmit and receive signals to obtain image data of the imaging region, wherein the acoustic transducer array comprises a plurality of transmit/receive pairs of transducer elements, and wherein one or more obstructions are positioned between the acoustic transducer array and at least a portion of the imaging region;
    determining a position of the one or more obstructions in the image data;
    computing, based on the determined position of the one or more obstructions in the image data an angular spectrum for the acoustic transducer array with respect to the imaging region in the presence of the one or more obstructions;
    determining an inverse filter for the acoustic transducer array based on the computed angular spectrum for the acoustic transducer array
    producing an ideal angular spectrum for the acoustic transducer array with respect to the imaging region which would exist in the absence of the one or more obstructions by multiplying the inverse filter by the angular spectrum for the acoustic array;
    weighting the signals produced by each transmit/receive pair of elements in the acoustic transducer array by a value of the inverse filter corresponding to an angular frequency of the transmit/receive pair; and
    producing an image of the imaging region by summing the weighted signals of all the transmit/receive pairs.

2. The method of claim 1, wherein employing the acoustic transducer array to produce the image data for the imaging region comprises performing a synthetic aperture acquisition.

3. The method of claim 1, further comprising performing an RF data (pre-detection) based or image based deconvolution algorithm.

4. The method of claim 1, further comprising
    determining an intensity of the image at points of interest within the imaging region by summing the weighted signals produced by each transmit/receive pair of elements in the acoustic transducer array from the point of interest.

5. The method of claim 4, wherein determining the inverse filter for the acoustic transducer array with respect to the point includes employing a ray tracing algorithm to compute an effective aperture seen by the point.

6. The method of claim 1, further comprising:
    determining at least one apodization function from the inverse filter for the acoustic transducer array with respect to the imaging region; and
    using the at least one apodization function to perform at least one transmit and receive operation.

7. The method of claim 6, wherein the at least one apodization function are determined from the inverse filter for the acoustic transducer array with respect to the imaging region by employing a decomposition algorithm.

8. An apparatus for imaging an imaging region, the apparatus comprising:
    an acoustic transducer array configured send and receive acoustic signals to produce image data for the imaging region, wherein the acoustic transducer array comprises a plurality of transmit/receive pairs of transducer elements, and
    one or more processors which, when the acoustic transducer array is positioned such that at least one or more obstructions exists between the transducer array and at least a portion of the imaging region, are configured to:
        determine a position of the one or more obstructions in the image data;
        compute, based on the determined position of the one or more obstructions in the image data, an angular spectrum for the acoustic transducer array with respect to the imaging region in the presence of the one or more obstruction;
        determine an inverse filter for the acoustic transducer array based on the computed angular spectrum for the acoustic transducer array
        produce an ideal angular spectrum for the acoustic transducer array with respect to the imaging region which would exist in the absence of the one or more obstructions by multiplying the inverse filter by the angular spectrum for the acoustic transducer array;
        weight a signal produced by each transmit/receiver pair of elements in the acoustic transducer array by a value of the inverse filter corresponding to an angular frequency of the transmit/receive pair; and
        produce an image of the imaging region by summing the weighted signals of all the transmit/receive pairs.

9. The apparatus of claim 8, wherein the apparatus is configured to produce the image data by performing a synthetic aperture acquisition.

10. The apparatus of claim 8, wherein the one or more processors are further configured to determine
an intensity of the image at a point of interest by summing the weighted signals produced by each transmit/receive pair of elements in the acoustic transducer array from the point of interest.

11. The apparatus of claim 8, wherein the inverse filter is determined based on an array of virtual transducers generated from the acoustic transducer array.

12. The apparatus of claim 8, wherein the one or more processors are configured to perform an RF data (pre-detection) based or image based deconvolution algorithm.

13. The apparatus of claim 8, wherein the one or more processors are configured to:
determine at least one apodization functions from the inverse filter for the acoustic transducer array with respect to the imaging region; and
perform at least one transmit and receive operation using the at least one apodization function.

14. The apparatus of claim 13, wherein the one or more processors are configured to determine the at least one apodization functions by employing a decomposition algorithm.

* * * * *